(12) United States Patent
Korzinov

(10) Patent No.: US 7,941,207 B2
(45) Date of Patent: *May 10, 2011

(54) CARDIAC MONITORING

(75) Inventor: Lev Korzinov, San Diego, CA (US)

(73) Assignee: CardioNet, Inc., San Diego, CA (US)

( * ) Notice: Subject to any disclaimer, the term of this patent is extended or adjusted under 35 U.S.C. 154(b) by 1104 days.

This patent is subject to a terminal disclaimer.

(21) Appl. No.: 11/674,053

(22) Filed: Feb. 12, 2007

(65) Prior Publication Data

US 2007/0129642 A1    Jun. 7, 2007

Related U.S. Application Data

(63) Continuation of application No. 10/762,887, filed on Jan. 21, 2004, now Pat. No. 7,194,300.

(51) Int. Cl.
*A61B 5/04* (2006.01)

(52) U.S. Cl. .......................................... 600/518

(58) Field of Classification Search .......... 600/509–521; 607/25
See application file for complete search history.

(56) References Cited

U.S. PATENT DOCUMENTS

| | | | |
|---|---|---|---|
| 4,621,617 A * | 11/1986 | Sharma | 600/16 |
| 4,622,979 A | 11/1986 | Katchis et al. | |
| 4,630,204 A | 12/1986 | Mortara | |
| 4,920,489 A | 4/1990 | Hubelbank et al. | |
| 4,938,228 A | 7/1990 | Righter et al. | |
| 4,951,681 A | 8/1990 | Mortara | |
| 4,958,641 A | 9/1990 | Digby et al. | |
| 4,977,899 A | 12/1990 | Digby et al. | |
| D326,716 S | 6/1992 | Mortara | |
| 5,191,891 A | 3/1993 | Righter | |
| 5,197,479 A | 3/1993 | Hubelbank et al. | |
| 5,226,425 A | 7/1993 | Righter | |
| 5,365,935 A | 11/1994 | Righter et al. | |
| 5,421,342 A | 6/1995 | Mortara | |
| 5,423,863 A | 6/1995 | Felblinger et al. | |
| 5,456,261 A | 10/1995 | Luczyk | |
| 5,490,515 A | 2/1996 | Mortara | |
| 5,522,396 A | 6/1996 | Langer et al. | |
| 5,546,950 A | 8/1996 | Schoeckert et al. | |

(Continued)

FOREIGN PATENT DOCUMENTS

JP    10-234688    9/1998

(Continued)

OTHER PUBLICATIONS

Biomedical Computer Laboratory, Institute for Biomedical Computing, Washington University, "Progress Report No. 21," Jul. 1, 1984-Jun. 30, 1985, 164 pages.

(Continued)

*Primary Examiner* — George Manuel
(74) *Attorney, Agent, or Firm* — Fish & Richardson P.C.

(57) ABSTRACT

Systems and techniques for monitoring cardiac activity. In one aspect, a method includes collecting information describing the variability in heart rate over a series of beats, designating variability at a lower end of physiological values as being largely irrelevant to atrial fibrillation, designating variability in a midrange of physiological values as being indicative of atrial fibrillation, designating variability in an upper range of physiological values as being negatively indicative of atrial fibrillation, and determining a relevance of the variability described in the collection to atrial fibrillation.

25 Claims, 7 Drawing Sheets

U.S. PATENT DOCUMENTS

| | | | |
|---|---|---|---|
| 5,581,369 | A | 12/1996 | Righter et al. |
| D377,983 | S | 2/1997 | Sabri et al. |
| 5,634,468 | A | 6/1997 | Platt et al. |
| 5,678,562 | A | 10/1997 | Sellers |
| 5,704,351 | A | 1/1998 | Mortara et al. |
| 5,730,143 | A | 3/1998 | Schwarzberg |
| 5,840,038 | A | 11/1998 | Xue et al. |
| 5,931,791 | A | 8/1999 | Saltzstein et al. |
| 5,959,529 | A | 9/1999 | Kail, IV |
| D414,870 | S | 10/1999 | Saltzstein et al. |
| 5,966,692 | A | 10/1999 | Langer et al. |
| 5,987,352 | A | 11/1999 | Klein et al. |
| 6,102,856 | A | 8/2000 | Groff et al. |
| 6,178,347 | B1 | 1/2001 | Olsson |
| 6,225,901 | B1 | 5/2001 | Kail, IV |
| 6,226,599 | B1 | 5/2001 | Namiki |
| 6,269,263 | B1 | 7/2001 | Ohnishi et al. |
| 6,287,252 | B1 | 9/2001 | Lugo |
| 6,289,243 | B1 | 9/2001 | Lin et al. |
| 6,308,094 | B1 | 10/2001 | Shusterman et al. |
| 6,366,871 | B1 | 4/2002 | Geva |
| 6,490,479 | B2 | 12/2002 | Bock |
| 6,496,731 | B1 | 12/2002 | Lovett |
| 6,564,077 | B2 | 5/2003 | Mortara |
| 6,569,095 | B2 | 5/2003 | Eggers |
| 6,664,893 | B1 | 12/2003 | Eveland et al. |
| 6,697,655 | B2 | 2/2004 | Sueppel et al. |
| 6,871,089 | B2 | 3/2005 | Korzinov et al. |
| 6,922,584 | B2 | 7/2005 | Wang et al. |
| 7,187,965 | B2 | 3/2007 | Bischoff et al. |
| 7,222,054 | B2 | 5/2007 | Geva |
| 7,311,665 | B2 | 12/2007 | Hawthorne et al. |
| 7,542,878 | B2 | 6/2009 | Nanikashvili |
| 7,693,574 | B2 | 4/2010 | Wessels |
| 2002/0065473 | A1 | 5/2002 | Wang et al. |
| 2002/0067256 | A1 | 6/2002 | Kail, IV |
| 2002/0128804 | A1 | 9/2002 | Geva |
| 2002/0193838 | A1 | 12/2002 | Lovett |
| 2003/0028442 | A1 | 2/2003 | Wagstaff et al. |
| 2003/0069486 | A1 | 4/2003 | Sueppel et al. |
| 2003/0069487 | A1 | 4/2003 | Mortara |
| 2003/0093125 | A1 | 5/2003 | Zhu et al. |
| 2003/0122677 | A1 | 7/2003 | Kail, IV |
| 2003/0144597 | A1 | 7/2003 | Bock |
| 2003/0172940 | A1 | 9/2003 | Rogers et al. |
| 2004/0010201 | A1 | 1/2004 | Korzinov et al. |
| 2004/0085186 | A1 | 5/2004 | Eveland et al. |
| 2005/0113703 | A1 | 5/2005 | Farringdon et al. |
| 2005/0113705 | A1 | 5/2005 | Fischell et al. |
| 2005/0119833 | A1 | 6/2005 | Nanikashvili |
| 2005/0203349 | A1 | 9/2005 | Nanikashvili |
| 2006/0010201 | A1 | 1/2006 | Korzinov |
| 2007/0100213 | A1 | 5/2007 | Dossas et al. |

FOREIGN PATENT DOCUMENTS

| | | |
|---|---|---|
| JP | 2002-301039 | 10/2002 |
| JP | 2004-517677 | 6/2004 |
| JP | 2005-523785 | 8/2005 |
| WO | WO 02/056961 A2 | 7/2002 |
| WO | WO 02/085200 A2 | 10/2002 |
| WO | WO 02/085201 A1 | 10/2002 |
| WO | WO 02/086792 A2 | 10/2002 |
| WO | WO 02/086793 A2 | 10/2002 |
| WO | WO 02/086835 A1 | 10/2002 |
| WO | WO 02/086837 A1 | 10/2002 |
| WO | WO 03/077752 A1 | 9/2003 |
| WO | WO 03/077755 | 9/2003 |

OTHER PUBLICATIONS

Savi Wireless—Mobile Cardiac Telemetry Brochure, published by at least May 2009, 12 Pages, Medicomp, Melbourne, Florida.

Extended European Search Report in Application No./Patent No. 05711728.5-2305/1706031—PCT/US2005/001849 mailed on Mar. 4, 2010, 13 pages.

Cerutti, S. et al., "Analysis of the Dynamics of RR Interval Series for the Detection of Atrial Fibrillation Episodes," Department of Biomedical Engineering, Polytechnic University, Milano Italy, Computers in Cardiology 1997, vol. 24, pp. 77-80.

Canadian Office Action dated May 21, 2009.

Japanese Office Action in Japanese Patent Application No. 2006-547636 dated Jun. 26, 2009 with an uncertified translation.

Description of Telephone Discussion with Examiner at the Japanese Patent Office who is examining Japanese Patent Application No. 2006-547636 (Japanese Appeal No. 2010-4938) (2 pages).

Machine translation of JP 10-234688 from Patent Abstracts of Japan (7 pages).

Cerutti et al., Analysis of the dynamics of RR interval series for the detection of atrial fibrillation episodes, Computers in Cardiology, pp. 77-80 (1997).

Description of Telephone Discussion with Examiner at the Japanese Patent Office who is examining Japanese Patent Application No. 2006-547636 (Japanese Appeal No. 2010-4938) (2 pages).

Machine translation of JP 10-234688 from Patent Abstracts of Japan (7 pages).

\* cited by examiner

CARDIAC MONITORING

CROSS-REFERENCE TO RELATED APPLICATIONS

This application claims the priority of U.S. application Ser. No. 10/762,887, filed on Jan. 21, 2004, now U.S. Pat. No. 7,194,300 as a continuation application. The contents of U.S. application Ser. No. 10/762,887 are incorporated herein by reference.

BACKGROUND

The following description relates to cardiac monitoring, for example, by monitoring cardiac electrical activity.

The electrical activity of the heart can be monitored to track various aspects of the functioning of the heart. Given the volume conductivity of the body, electrodes on the body surface or beneath the skin often display potential differences related to this activity. Anomalous electrical activity can be indicative of disease states or other physiological conditions that can range from benign to deadly.

One example of such a physiological condition is atrial fibrillation. Atrial fibrillation involves the loss of synchrony between the atria and the ventricles. In complex atrial fibrillation, long-lived wavelets of depolarization travel along circular paths in the atria. This can lead to irregular ventricular beating as well as blood stagnation and clotting in the atria.

Atrial fibrillation is among the most common forms of cardiac arrhythmia and may affect more than two million people annually. Atrial fibrillation has been associated with stroke, congestive heart failure, and cardiomyopathy.

Another example of such a physiological condition is atrial flutter. Atrial flutter also involves the loss of synchrony between the atria and the ventricles. In atrial flutter, multiple atrial waveforms reach the atrioventricular (AV) node during each ventricular beat due to, e.g., atrial scars, an atrial infarction, or a re-entrant circuit encircling a portion of the right atrium.

Atrial flutter is less common than atrial fibrillation but is also associated with stroke, congestive heart failure, and cardiomyopathy.

SUMMARY

The cardiac monitoring systems and techniques described here may include various combinations of the following features.

A method can include determining a beat-to-beat variability in cardiac electrical activity; determining a relevance of the variability to one of atrial fibrillation and atrial flutter using a non-linear statistics, identifying one of an atrial fibrillation event and an atrial flutter event based on the determined relevance. The event is a period in time when the information content of the cardiac electrical activity is of increased relevance.

The end of the event can be identified based on the determined relevance. An event state associated with atrial fibrillation can be transitioned into in response to identification of the event. The event can be transmitted to a remote receiver from an ambulatory patient. The relevance of the variability to atrial fibrillation can be determined by receiving information identifying a ventricular beat and assigning a preset value indicating that the variability is negatively indicative of atrial fibrillation.

A ventricular tachycardia event can be identified based at least in part on the information identifying the ventricular beat. The relevance of the variability to atrial fibrillation can be determined by determining an average relevance of variability in a collection of R to R intervals.

The beat-to-beat variability can be determined in a series of successive beats, e.g., by determining the variability in an interval between successive R-waves. The event can be identified by comparing the relevance of the variability to a first predetermined amount of relevance. Further, the relevance of the variability in the event can be compared to a second predetermined amount of relevance to identify the end of the event. The second predetermined amount can be lower than the first predetermined amount.

A method can include collecting information describing the variability in heart rate over a series of beats, designating variability at a lower end of physiological values as being largely irrelevant to atrial fibrillation, designating variability in a midrange of physiological values as being indicative of atrial fibrillation, designating variability in an upper range of physiological values as being negatively indicative of atrial fibrillation, and determining a relevance of the variability described in the collection to atrial fibrillation.

The variability can be designated by multiplying the information describing the variability by a weighting factor. Information describing a variability in R to R intervals over a series of beats can be collected. The collected information can be a function of a ratio of a first R to R interval and an immediately preceding R to R interval, such as information related to factor DRR(n) as given by $$DRR(n) = ABS\left(\frac{RR(n, n-1)}{RR(n, n-1) + RR(n-1, n-2)} - \frac{1}{2}\right).$$

The variability at the lower end of physiological values can be designated as being largely irrelevant by designating information related to factors DRR(n) less than about 0.0.2 as being largely irrelevant. The variability at the midrange of physiological values can be designated as being indicative of atrial fibrillation by designating information related to factors DRR(n) greater than about 0.02 and less than about 0.15 as being indicative of atrial fibrillation. The variability at the upper range of physiological values can be designated as being negatively indicative of atrial fibrillation by designating information related to factors DRR(n) greater than about 0.157 as being negatively indicative of atrial fibrillation.

Information describing the variability can be collected by collecting the variability in heart rate over a series of between 20 and 200 of the recent R to R intervals. The determined relevance of the variability can be the relevance of the variability to sustained atrial fibrillation. The series of R to R intervals can be a continuous series of R to R intervals.

A method can include comparing recent R to R intervals with preceding R to R intervals to yield a collection of comparisons, weighting the comparisons according to a likelihood that the comparisons are relevant to atrial fibrillation, and determining the average relevance of the collection to atrial fibrillation. The weighting can include identifying a first of the recent beats as a ventricular beat and assigning a preset value to weight the first beat in the collection. The preset value can be negatively indicative of atrial fibrillation.

The comparisons can be weighted by designating variability at a lower end of physiological values as being largely irrelevant to atrial fibrillation and designating variability in a midrange of physiological values as being indicative of atrial fibrillation. The comparisons can also be weighted by designating variability in an upper range of physiological values as being negatively indicative of atrial fibrillation. A ventricular tachycardia event can be identified based at least in part on the identification of the ventricular beat. Recent R to R intervals can be compared with immediately preceding R to R intervals to yield a collection of comparisons.

The cardiac monitoring systems and techniques may provide one or more of the following advantages. Atrial fibrillation ("AFib") and/or atrial flutter ("AFlut," with "AF" referring to either) can be distinguished from other types of cardiac arrhythmia, such as the normal sinus rhythm irregularity, irregularity from various types of heart blocks, and the irregularity associated with premature ventricular contractions. The described systems and techniques are a practical approach to calculating the beat-to-beat irregularity while providing improved positive predictability of AF. Moreover, the described systems and techniques are able to identify sustained AF episodes, where AF continues for more that approximately 20 beats and has an increased clinical significance.

For example, when the systems and techniques described here were used to analyze the MIT-BIH arrhythmia database, available from MIT-BIH Database Distribution, MIT Room E25-505A, Cambridge, Mass. 02139, USA, a sensitivity to AF in excess of 90% and a positive predictivity in excess of 96% were obtained.

The described systems and techniques are well-adapted to monitoring cardiac signals of ambulatory patients who are away from controlled environments such as hospital beds or treatment facilities. The cardiac signals obtained from to ambulatory patients may be noisier and otherwise strongly impacted by the patients' heightened levels of activity. Thus, improved monitoring systems and techniques, such as those described herein, are required for ambulatory patients.

The described systems and techniques are also well-adapted to real-time monitoring of arrhythmia patients, where minimal delays in distinguishing between different types of cardiac arrhythmia can speed the delivery of any urgent medical care. The described systems and techniques also require minimal computational resources. Further, the described systems and techniques do not require training before different types of cardiac arrhythmia can be distinguished.

The details of one or more implementations of the invention are set forth in the accompanying drawings and the description below. Other features, objects, and advantages will be apparent from the description and drawings, and from the claims.

DESCRIPTION OF DRAWINGS

Like reference symbols in the various drawings indicate like elements.

DETAILED DESCRIPTION

Figure 1:
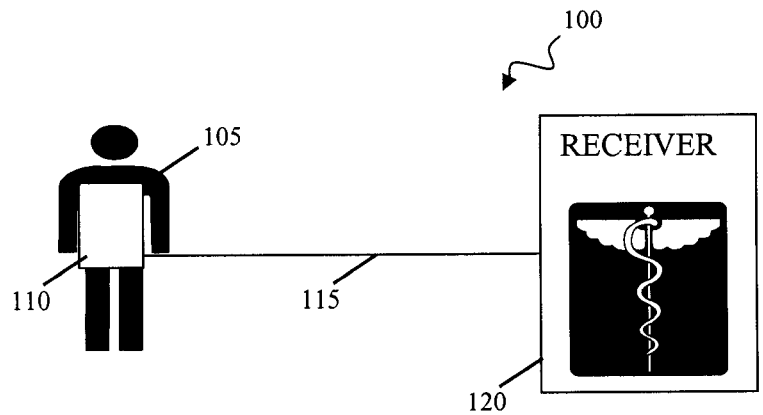
FIG. 1 shows a system in which a cardiac signal is monitored for medical purposes.

FIG. 1 shows a system 100 in which a cardiac signal is monitored for medical purposes. System 100 includes an individual 105, instrumentation 110, a signal path 115, and a receiver 120. Individual 105 can be a patient or a healthy individual for whom monitoring of one or more biological signals is deemed to be appropriate. Instrumentation 10 can include one or more sensing, calibration, signal processing, control, data storage, and transmission elements suitable for generating and processing the cardiac signal, as well as relaying all or a portion of the cardiac signal over path 115. Path 115 can be any suitable medium for data transmission, including wired and wireless media suitable for carrying optical and/or electrical signals. The receiver 120 can include a receiver element for receiving the transmitted signal, as well as various data processing and storage elements for extracting and storing the information carried by the transmission regarding the state of individual 105. The receiver 120 can be a medical system in that receiver 120 presents information to medical personnel or to a medical expert system for analysis. The receiver 120 either can reside remotely from instrumentation 110 in that receiver 120 is not located at the same site as instrumentation 110 (e.g., at the same hospital, nursing home, or other medical care facility) or the receiver 120 can reside within the same general area or vicinity as instrumentation 110 (e.g., within the same room, building, or health care facility).

Figure 2:
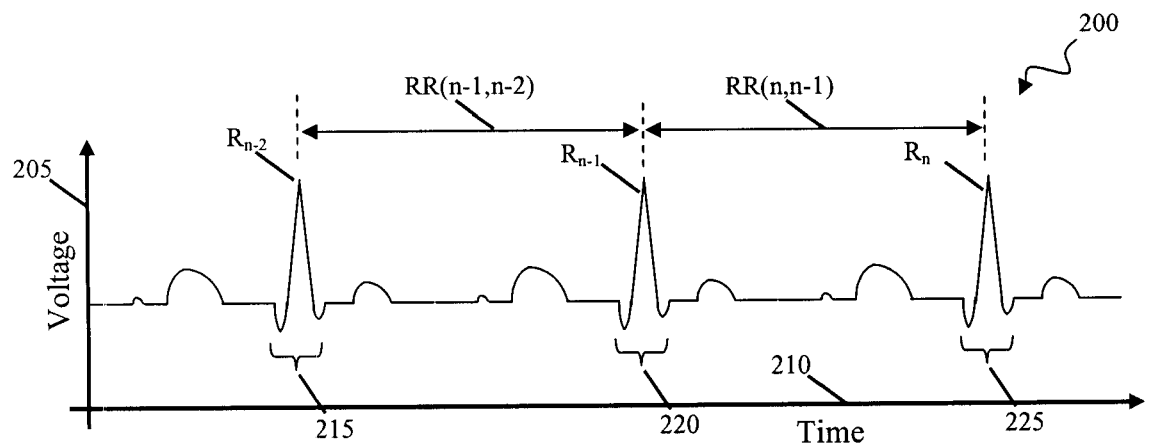
FIG. 2 shows an example of a cardiac signal.

FIG. 2 shows an example of a cardiac signal, namely the trace of a scalar electrocardiogram 200. Electrocardiogram trace 200 follows a potential difference 205 measured between two points on the body surface of an individual. Potential difference 205 changes with time 210 in a manner characteristic of the physiology and function of an individual's heart.

Electrocardiogram trace 200 generally includes features characteristic with particular aspects of cardiac activity. For example, trace 200 includes a series of QRS complexes 215, 220, 225 associated with activation of the ventricles. QRS complex 225 includes an R-wave $R_n$, QRS complex 220 includes an R-wave $R_{n-1}$, and QRS complex 215 includes an R-wave $R_{n-2}$. The time between successive R-waves can be referred to as the R to R interval. In particular, the R to R interval between R-wave $R_n$ and R-wave $R_{n-1}$ is RR(n,n−1) and the R to R interval between R-wave $R_{n-1}$ and R-wave $R_{n-2}$ is RR(n−1,n−2).

Figure 3:
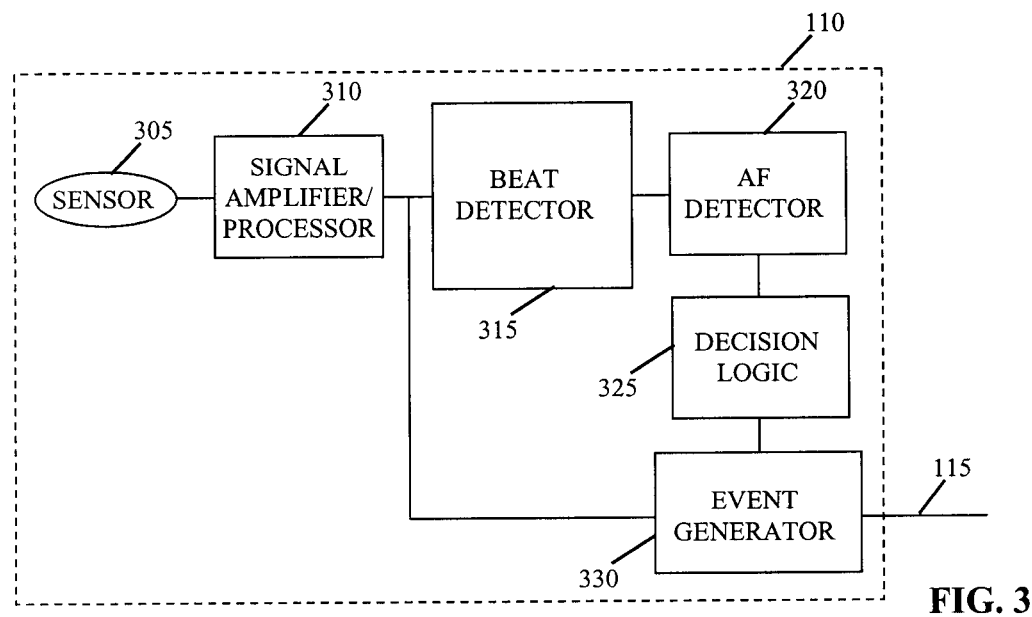
FIG. 3 shows an example of instrumentation for cardiac monitoring using a cardiac signal.

FIG. 3 shows an example of instrumentation 110 for cardiac monitoring using a cardiac signal such as electrocardiogram trace 200. Instrumentation 110 includes a sensor 305, a signal amplifier/processor 310, a beat detector 315, an atrial fibrillation/atrial flutter (AF) detector 320, decision logic 325, and an event generator 330. Sensor 305 can include two or more electrodes subject to one or more potential differences that yield a voltage signal such as electrocardiogram trace 200. The electrodes can be body surface electrodes such as silver/silver chloride electrodes and can be positioned at defined locations to aid in monitoring the electrical activity of the heart. Sensor 305 can also include leads or other conductors that form a signal path to signal amplifier/processor 310. Signal amplifier/processor 310 can receive, amplify, and/or process the voltage signals. The processing can include filtering and digitization. The amplification and remainder of the processing can occur before or after digitization. Signal amplifier/processor 310 can provide the amplified and/or processed signal to beat detector 315.

Beat detector 315 is a device such as a circuit or other arrangement that identifies the time period between ventricular contractions. For example, beat detector 315 can be a QRS detector in that it identifies successive QRS complexes (or an equivalent indicator of ventricular activity) and determines the beat-to-beat timing from the time between complexes. The beat-to-beat timing can be determined by measuring times between successive R-waves, such as RR(n,n−1) and RR(n−1,n−2) in electrocardiogram trace 200 (FIG. 2). Beat detector 315 can provide information regarding the time period between ventricular contractions to AF detector 320.

AF detector 320 is a data processing device that analyzes information regarding the time period between ventricular contractions to detect AF. The detection of AF can include distinguishing AF from other sources of ventricular irregularity, such as premature ventricular contraction, heart blocks, and normal sinus rhythm irregularity. The detection of AF can also include distinguishing between short AF episodes and sustained AF episodes. Short AF episodes generally include between two and 20 beats and may or may not have clinical significant, whereas sustained AF episodes generally include more than 20 beats and may have relatively greater clinical significance. The detection of AF can also include the detection of other types of irregularity caused by random refractory periods of the ventricles.

AF detector 320 can analyze information regarding the time period between ventricular contractions to detect AF using non-linear statistical approaches. Non-linear statistics treats the relationship between variables as something other than a linear function. Detail regarding an example non-linear statistical approach to detecting AF is given below. AF detector 320 can provide information regarding the detection of AF to decision logic 325

Decision logic 325 is a set of instructions for determining when the AF detected by AF detector 320 has commenced and terminated. For example, decision logic 325 can be embodied in a circuit or decision logic 325 can be executed by a data processing device such as AF detector 320. Decision logic 325 can also trigger the generation of an AF event by event generator 230.

Event generator 330 is a device such as a data processing device that prepares an AF event for handling. An AF event is a period in time when the information content of the signal sensed by sensor 305 is deemed to be of increased relevance to the monitoring of AF. AF events need not be of equal or predetermined duration. For example, an event associated with an sustained AF episode may have a longer duration than an event associated with a short AF episode.

Event generator 330 can prepare an AF event for handling by collecting information that summarizes the relevance of the event to the detection and/or monitoring of AF. For example, event generator 330 can excise data associated with the period identified as AF from the amplified and processed signal output from signal amplifier/processor 310. Event generator 330 can also redact such data (e.g., by selecting the first three minutes worth when generating the event). Handling the AF event can include transmitting the AF event over data link 115 or storing the AF event in a data storage device.

Figure 4:
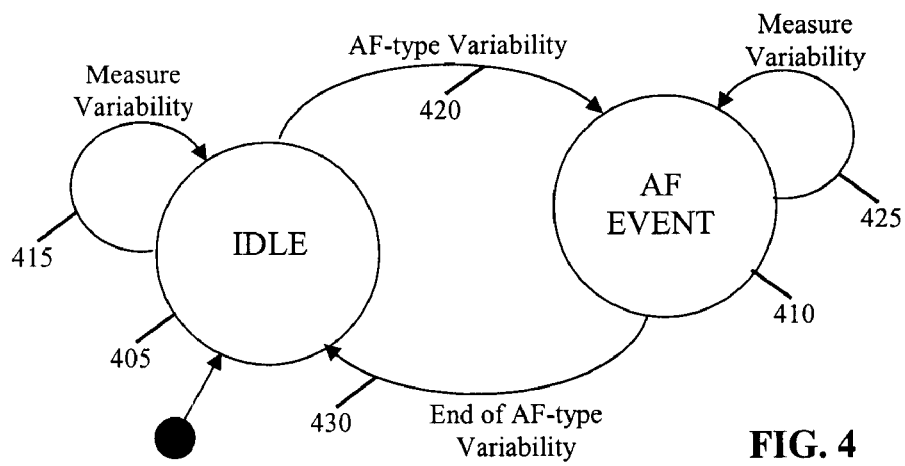
FIG. 4 shows an example state diagram of a cardiac monitoring system during cardiac monitoring.

FIG. 4 shows an example state diagram 400 of a cardiac monitoring system during cardiac monitoring. For example, state diagram 400 can relate to the operation of an assembly such as AF detector 320 and decision logic 325 in instrumentation 110 (FIG. 3). State diagram 400 includes an idle state 405 and an AF event state 410. Idle state 405 originates a reflexive transition 415 and a state transition 420. AF event state 410 originates a reflexive transition 425 and a state transition 430. Reflexive transition 415 is associated with a series of variability measurements. State transition 420 is triggered by the onset of AF-type variability as detected by such measurements. Reflexive transition 425 is associated with another series of variability measurements. State transition 430 is triggered by the end of AF-type variability as detected by such measurements.

In operation, a cardiac monitoring system can start in idle state 405 and measure the variability of a cardiac signal. For example, the system can measure the variability in the beat-to-beat timing of successive R-waves, such as the variability between RR(n,n−1) and RR(n−1,n−2) in electrocardiogram trace 200 (FIG. 2). Once the variability has been identified as AF-type variability, the system transitions to AF event state 410 where the system continues to measure the variability of the cardiac signal. In AF event state 410, once the AF-type variability has ended, the system returns to idle state 405.

Figure 5:
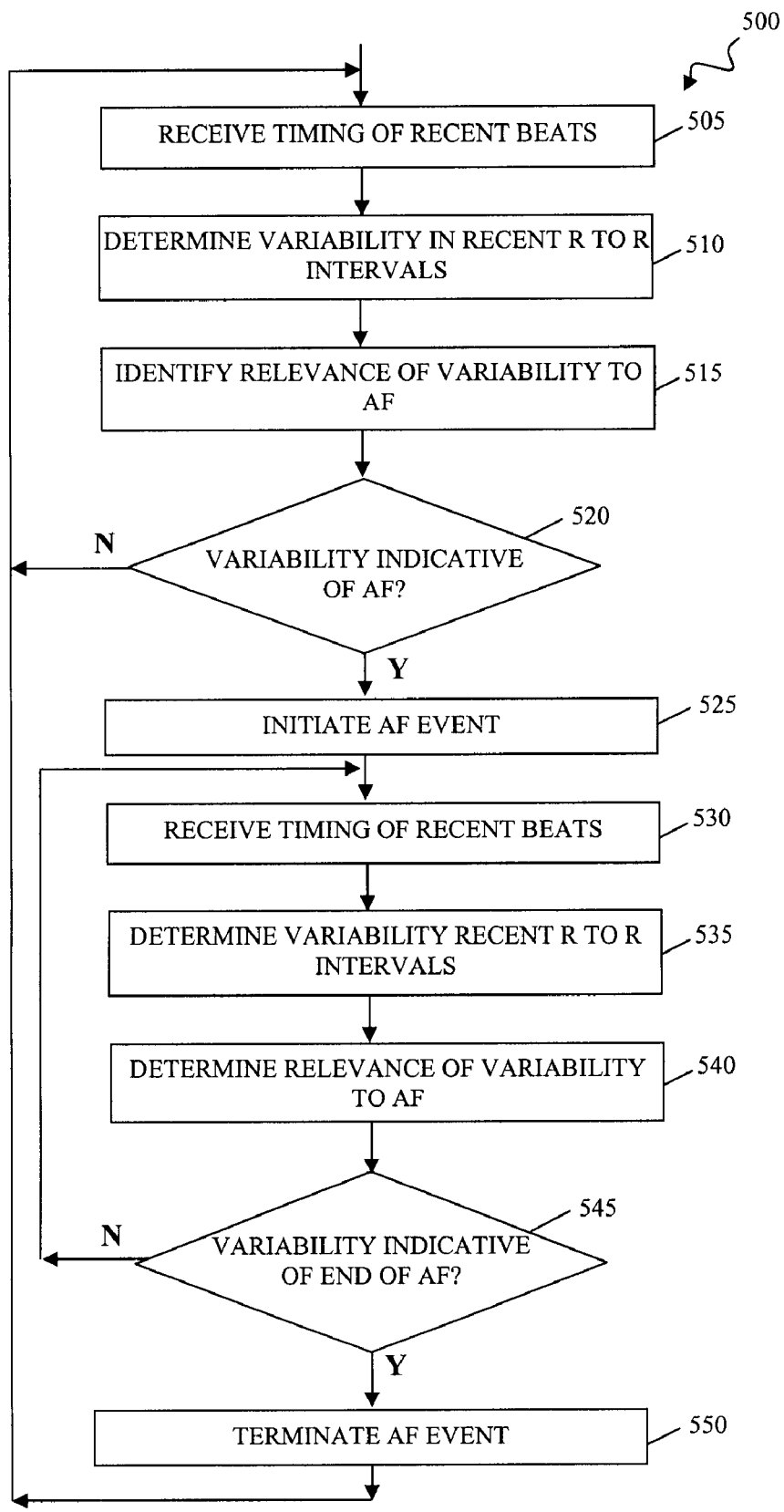
FIG. 5 shows a process for cardiac monitoring for the detection of an AF event.

FIG. 5 shows a process 500 for cardiac monitoring, e.g., for the detection of an AF event. Process 500 can be performed by one or more data processing devices that perform data processing activities. The activities of process 500 can be performed in accordance with the logic of a set of machine-readable instructions, a hardware assembly, or a combination of these and/or other instructions. The activities in process 500 can be performed at any of a number of different elements in a system in which a biological signal is monitored. For example, in instrumentation 110 (FIG. 3), the activities in process 900 can be performed at AF detector 320, decision logic 325, and event generator 330.

The device performing process 500 receives information regarding the timing of recent beats it 505. The timing information can be received in discrete amounts (e.g., on a beat-to-beat basis) or in a collection that includes such information. Using the received timing information, the system determines the variability in the recent R to R intervals at 510. The variability in the R to R intervals can reflect the beat-to-beat change in heart rate over a set period or over a set number of beats.

The system can also identify the relevance of such variability to AF at 515. The variability is relevant to AF when it is associated with a high probability that an individual undergoes AF at or near the time of the recent beats. Relevance can be identified by comparing the variability to a predetermined amount of variability or to an amount identified as typical for the monitored patient.

The system can also determine if the identified relevance of the variability is indicative of the monitored individual undergoing AF at decision 520. If not, the system returns to 505. This return can correspond to the system remaining in idle state 405 along reflexive transition 415 in state diagram 400 (FIG. 4). If the system determines that the results of the monitoring are indicative of the individual undergoing AF, the system initiates an AF event at 525. This initiation of the AF event can correspond to the system transitioning to AF event state 410 in state diagram 400 (FIG. 4). The initiation of such an event can include various activities that lead to the generation of an event, such as triggering an event generator to add markers to a data stream such as electrocardiogram trace 200 or excising a relevant portion of the data stream.

The system can continue to receive information regarding the timing of recent beats at 530. Using the received timing information, the system determines the variability in the recent R to R intervals at 535. The system can also identify the relevance of such variability to the end of AF at 540. The variability is relevant to the end of AF when it is associated with an increased probability that AF has halted. Relevance can be identified by comparing the variability to a predetermined amount of variability or to an amount identified as typical for the monitored patient.

The system can also determine if the identified relevance of the variability indicates that AF has ended in the monitored individual at decision 545. If not, the system returns to 530. This return can correspond to the system remaining in AF event state 410 along reflexive transition 425 in state diagram 400 (FIG. 4). If the system determines that AF has ended in the monitored individual, the system returns to 555. This return can correspond to the system transitioning to idle state 405 in state diagram 400 (FIG. 4).

Figure 6A:
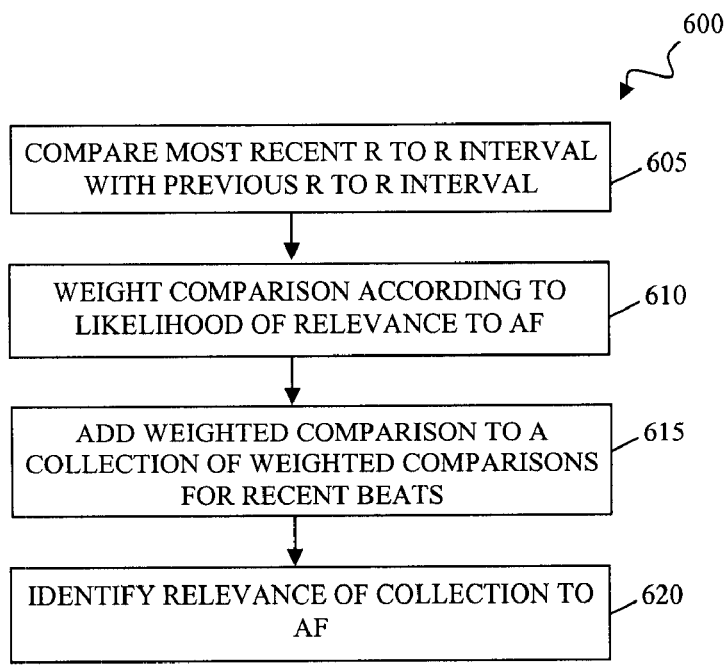
FIG. 6A shows a process for determining the variability in the recent R to R intervals and identifying if the variability is relevant to either the onset or termination of AF.

FIG. 6A shows a process 600 for determining the variability in the recent R to R intervals and identifying if the variability is relevant to either the onset or termination of AF. Process 600 can be performed independently or process 600 can be performed as part of a larger collection of activities. For example, process 600 can be performed as part of process 500, namely as steps 510, 515 or as steps 535, 540 (FIG. 5). Various activities in process 600 can also be performed to trigger state transitions 420, 430 in state diagram 400 (FIG. 4).

Figure 6B:
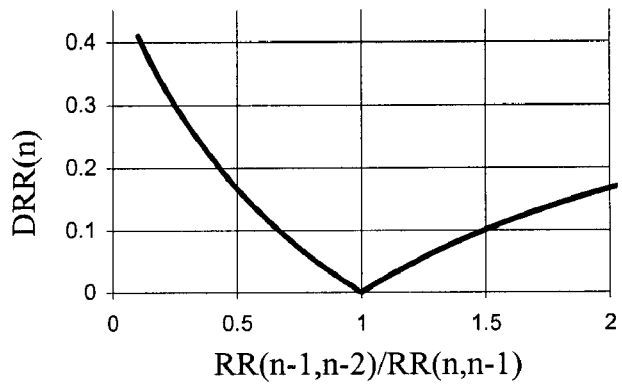
FIG. 6B shows a graph of factor DRR(n) as a function of RR(n−1,n−2)/RR(n,n−1).

The system performing process 600 can compare the most recent R to R interval (e.g., RR(n,n−1) of FIG. 2) with the immediately preceding R to R interval (e.g., RR(n−1,n−2) of FIG. 2) at 605. Such a comparison can yield a factor that reflects the beat-to-beat variability in heart rate. For example, a factor DRR(n), given by the expression $$DRR(n) = ABS\left(\frac{RR(n, n-1)}{RR(n, n-1) + RR(n-1, n-2)} - \frac{1}{2}\right) \quad \text{Equation 1}$$

can reflect the beat-to-beat variability in R to R interval and in heart rate. A graph of factor DRR(n) as a function of RR(n−1,n−2)/RR(n,n−1) is shown in FIG. 6B.

The system performing process 600 can also weight the comparison of the most recent R to R interval with the immediately preceding R to R interval according to the likelihood that the results of the comparison are indicative of AT at 610. The weighting can determine a role that the comparison will play in subsequent processing cardiac monitoring activities. For example, the weighting can include the whole or partial exclusion of a certain comparisons from subsequent cardiac monitoring activities.

Figure 7:
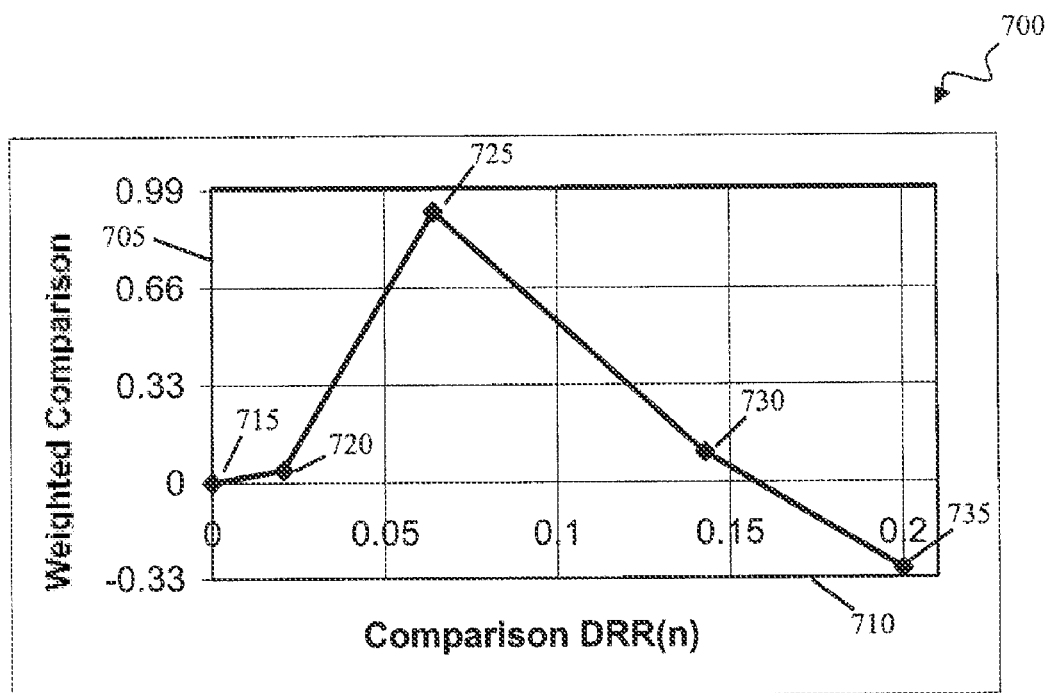
FIG. 7 shows a transformation function for weighting the variability in the timing of recent beats.

One technique for weighting the comparison is through the use of a transformation, such as transformation function 700 shown in FIG. 7. Transformation function 700 provides weights that are multiplied by the value of a comparison (e.g., factor DRR(n)) to reflect the relevance of the comparison to AF. The weights provided in transformation function 700 can be multiplied by the value of every comparison or by a selected subset of the comparisons. One technique for selecting such a subset is discussed further below.

Transformation function 700 is adapted to the factor DRR (n) given in equation 1. In particular, transformation function 700 is adapted to overweight factor DRR(n) when factor DRR(n) is in a midrange of potential physiological values (e.g., when DRR(n) is greater than about 0.02 and less than about 0.15). Transformation function 700 is adapted to weight factor DRR(n) as being negatively indicative of AF when factor DRR(n) is at the upper range of potential physiological values (e.g., when DRR(n) is greater than about 0.157). Transformation function 700 is adapted to weight factor DRR(n) as being largely irrelevant to AF when factor DRR(n) is at the lower range of potential physiological values (e.g., when DRR(n) is less than about 0.0.2). Transformation function 700 includes a scalar weighted comparison 705 that varies as a function of the comparison factor DRR(n) 710. In particular, weighted comparison 705 varies linearly between points 715, 720, 725, 730, 735. The values of points 715, 720, 725, 730, 735 are given in Table 1.

TABLE 1

| Point | Comparison DRR(n) | Weight Comparison |
| --- | --- | --- |
| 715 | 0 | 0 |
| 720 | 0.0206 | 0.0417 |
| 725 | 0.0642 | 0.9178 |
| 730 | 0.1427 | 0.1005 |
| 735 | 0.2 | −0.3 |

In operation, weighted comparison 705 for any value of the factor DRR(n) can be determined by linear interpolation between the weighted comparisons of points 715, 720, 725, 730, 735. The interpolation can be performed for each value of the factor DRR(n) as it arises or the results of a certain number of such interpolations can be stored in a look up table. For any value of the factor DRR(n) above 0.2, a weighted comparison of −0.3 can be assigned.

Returning to FIG. 6A, the system performing process 600 can also add a weighted comparison to a collection of weighted comparisons for recent beats at 615. For example, the system can form a FIFO stack or an array of weighted comparisons having a separate data element for each of between 10 and 200 (e.g., 100) of the most recent beats. The system can also determine the relevance of the collection of weighted comparisons for recent beats to AF at 620. The collection of weighted comparisons can be relevant to either the onset or termination of AF.

To determine the relevance, the system can sum the weighted comparisons to arrive at a number that represents the average relevance of the weighted comparisons in the collection. The system can calculate such sums for several beats in a row before determining that the beat-to-beat variability is indicative of the onset or termination of AF. In one implementation, the system calculates the average of the weighted comparisons of the beats in the collection and compares this average with a first predetermined threshold to determine if the variability is indicative of the onset of AF and with a second predetermined threshold to determine if the variability is indicative of the termination of AF. In general, the first, onset threshold may be higher than the second, termination threshold. The difference between the onset and termination thresholds can introduce hysteresis into the state transitions to stabilize any system performing process 600.

Figure 8:
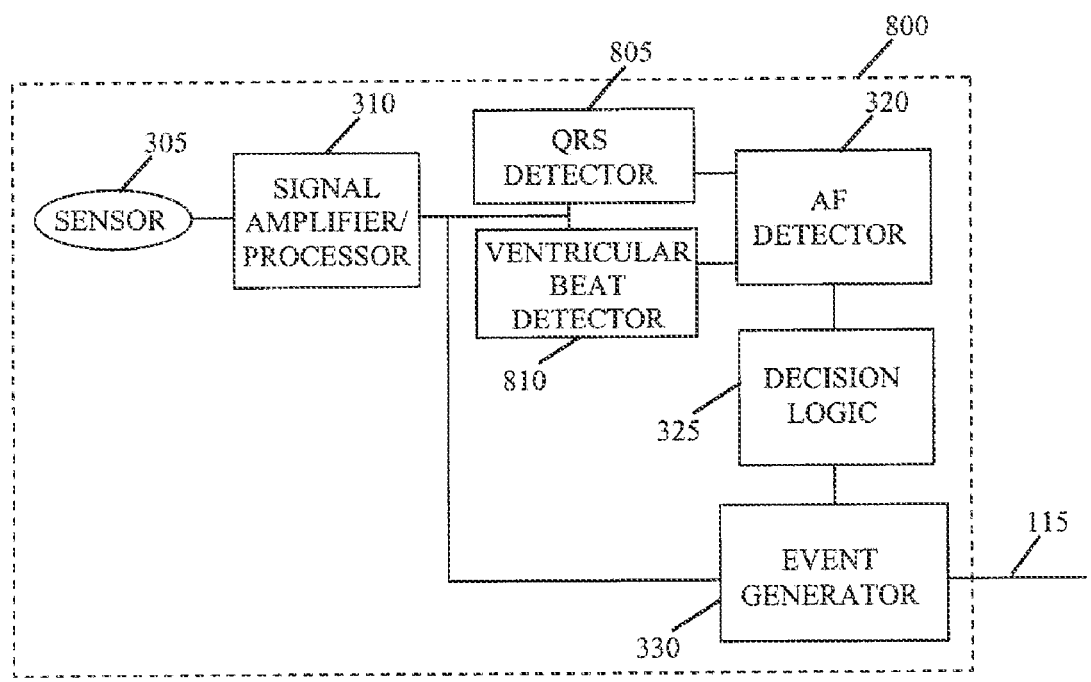
FIG. 8 shows an example of instrumentation for cardiac monitoring using an electrocardiogram trace.

FIG. 8 shows an example of instrumentation for cardiac monitoring using an electrocardiogram trace, namely instrumentation 800. In addition to sensor 305, signal amplifier/processor 310, AF (AF) detector 320, decision logic 325, and event generator 330, instrumentation 800 also includes a QRS detector 805 and a ventricular beat detector 810. QRS detector 805 and ventricular beat detector 810 can both receive an amplified and processed signal from signal amplifier/processor 310. QRS detector 805 is a device such as a circuit or other arrangement that identifies the time period between successive QRS complexes. QRS detector 805 can provide information regarding the time period between successive QRS complexes to AF detector 320

Ventricular beat detector 810 is a device such as a circuit or other arrangement that identifies ventricular beats. Ventricular beats (i.e., premature ventricular beats) are irregular beats that interrupt the normal heart rhythm. Ventricular beats generally arise from a ventricular focus with enhanced automaticity. Ventricular beats may also result from reentry within the His-Purkinje system. The occurrence of ventricular beats is generally unrelated to AF. For example, the occurrence of ventricular beats can be used to identify ventricular tachycardia (e.g., when there are three or more consecutive ventricular beats). Ventricular beats may be precipitated by factors such as alcohol, tobacco, caffeine, and stress. Ventricular beat detector 810 can monitor an electrocardiogram trace to identify ventricular beats. Various systems and techniques for identifying ventricular beats can be used. For example, the Mortara VERITAS Analysis Algorithm, available from Mortara Instrument, Inc. (Milwaukee, Wis.), can be used. Ventricular beat detector 810 can also provide information regarding the occurrence of ventricular beats to AF detector 320.

Ventricular beat detector 810 can be housed together with QRS detector 805. An example of such a joint device is the ELI 250TM Electrocardiograph available from Mortara Instrument, Inc. (Milwaukee, Wis.).

Figure 9:
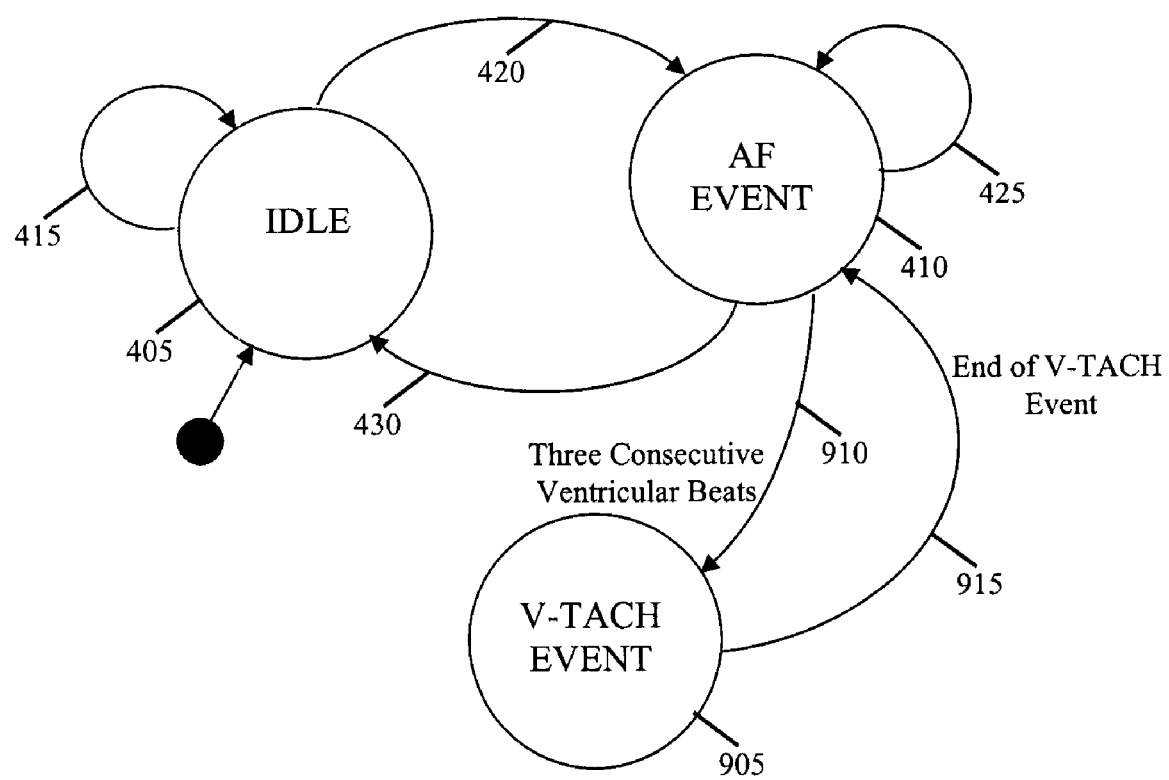
FIG. 9 shows an example state diagram of a cardiac monitoring system that accommodates the variability caused by ventricular beats.

Approaches for determining the variability in recent R to R intervals and identifying if the variability is relevant to either the onset or termination of AF can accommodate the variability caused by ventricular beats. FIG. 9 shows an example state diagram 900 of a cardiac monitoring system that accommodates the variability caused by ventricular beats. In addition to idle state 405 and AF event state 410, state diagram 900 also includes a ventricular tachycardia (V-TA CH) event state 905. Ventricular tachycardia is a rapid succession of ventricular contractions (e.g., between 140 and 220 per minute) generally caused by an abnormal focus of electrical activity in a ventricle. Ventricular tachycardia can last from a few seconds to several days and can be caused by serious heart conditions such as a myocardial infarction. AF event state 410 originates a state transition 910 that is triggered by the occurrence of three consecutive ventricular beats. V-TACH event state 905 originates a state transition 910 that is triggered by the end of a V-TACH event. The end of a V-TACH event can be identified, e.g., when the rate of ventricular contractions falls below a predetermined value (e.g., a value between 100 and 200 bpm).

Figure 10:
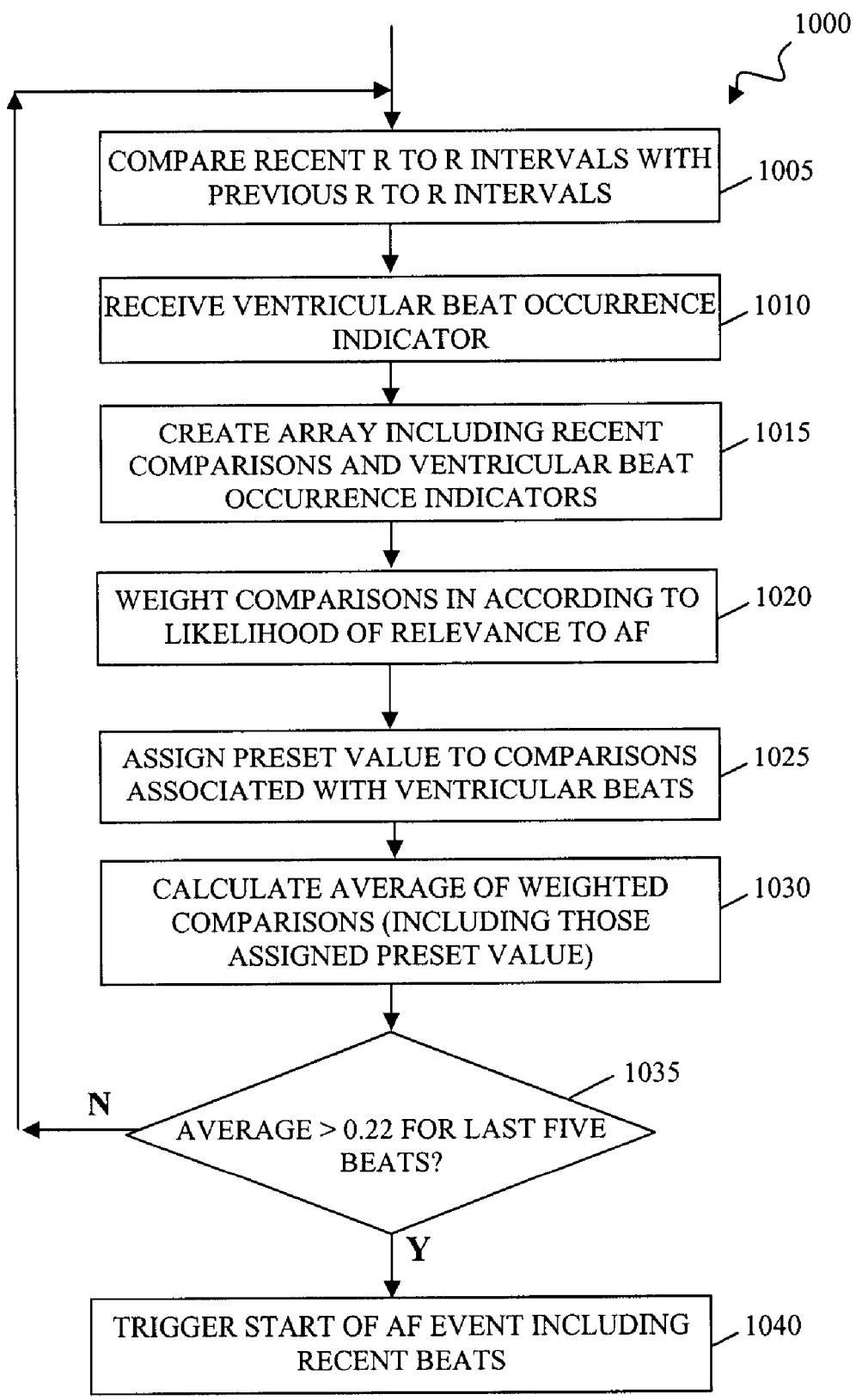
FIG. 10 shows a process for determining the variability of recent R to R intervals and identifying if the variability is relevant to the onset of AF while accommodating the variability caused by ventricular beats.

FIG. 10 shows a process for determining the variability in recent R to R intervals and identifying if the variability is relevant to the onset of AF while accommodating the variability caused by ventricular beats, namely a process 1000. Process 900 can be performed independently or process 1000 can be performed as part of a larger collection of activities. For example, process 1000 can be performed as part of process 500, namely as steps 510, 515 (FIG. 5). Various activities in process 1000 can also be performed to trigger state transition 420 in state diagram 900 (FIG. 9).

The system performing process 1000 can compare the recent R to R intervals with the respective, immediately-preceding R to R intervals at 1005 using, e.g., the expression in Equation 1 to reflect the beat-to-beat variability in heart rate. The system performing can also receive an indicator of the occurrence of a ventricular beat at 1010. Such an indicator can be received, e.g., from a ventricular beat detector.

The system can create an array or other data structure that includes both the ventricular beat indicators and the R to R interval comparisons at 1015. The array can include the ventricular beat indicators and the R to R interval comparisons for between 10 and 200 (e.g., 100) of the most recent beats. The system can also weight the comparisons according to the likelihood that the R to R interval comparisons are relevant to AF at 1020 using, e.g., transformation function 700 (FIG. 7).

The system can also assign a preset value to the R to R interval comparisons associated with ventricular beats at 1025. The preset value can be a penalty value in that the preset value reflects a decreased likelihood that the variability is indicative of an AF event. The preset value can be selected in light of the approaches used to compare the R to R intervals and to weight such comparisons. For example, when the R to R intervals are compared using Equation 1 and the resulting comparisons are weighted using transformation function 700 (FIG. 7), R to R interval comparisons associated with ventricular beats can be assigned a preset value of –0.06 and R to R intervals comparisons associated with the R to R intervals immediately succeeding ventricular beats can be assigned a preset value of zero.

Using both the weighted and preset timing comparisons, the system can calculate the average value of an entry in the array of the most recent beats at 1030. If the system determines that the average is greater than 0.22 for the last five beats at decision 1035, then the system triggers the start of an AF event in the recent beats at 1040. On the other hand, if the system determines that the average is less than or equal to 0.22 for the last five beats, then the system returns to compare the recent R to R intervals with the previous R to R interval at 1005.

Figure 11:
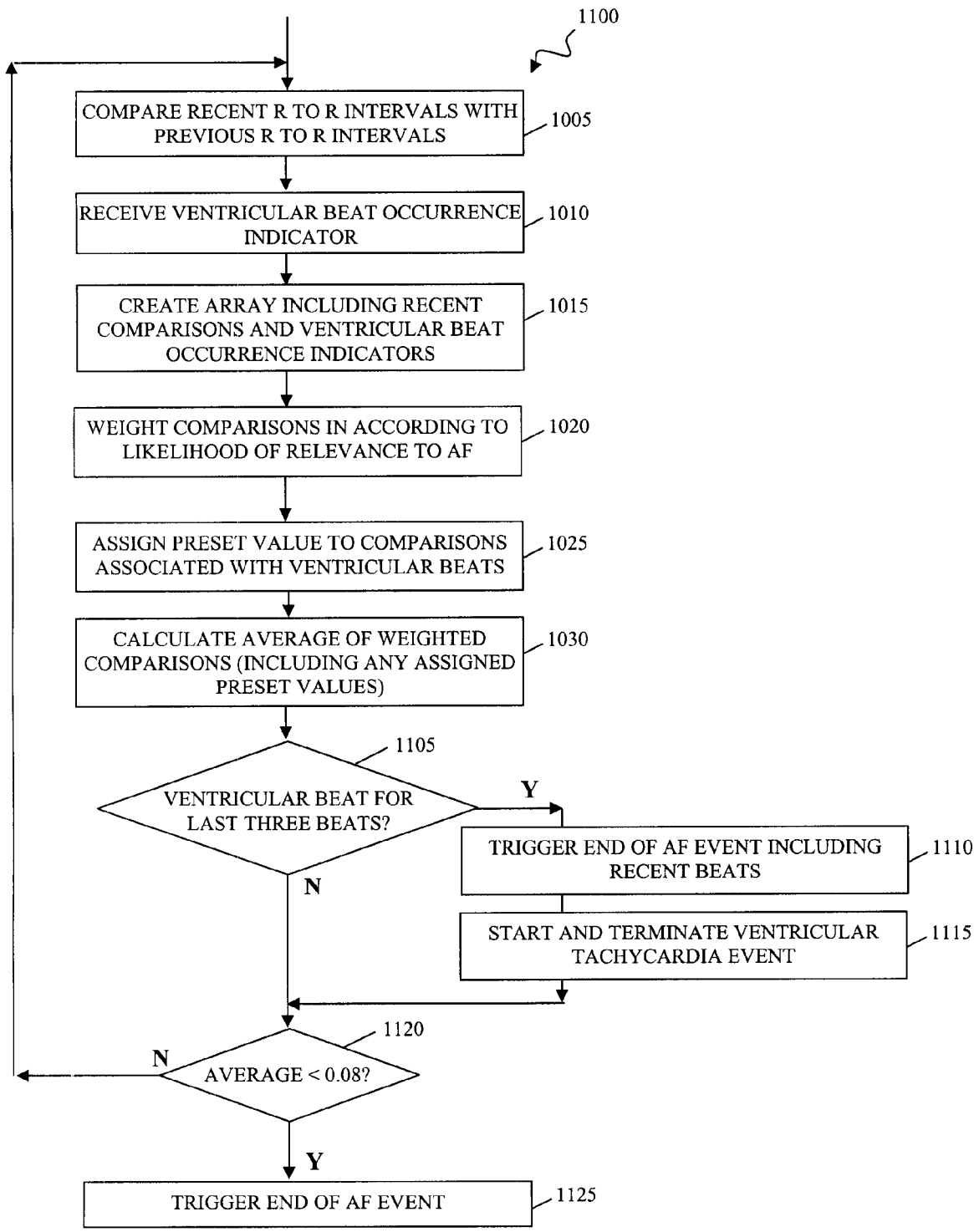
FIG. 11 shows a process for determining the variability in recent R to R intervals and identifying if the variability is relevant to the termination of AF while accommodating the variability caused by ventricular beats.

FIG. 11 shows a process for determining the variability in the recent R to R intervals and identifying if the variability is relevant to the termination of AF while accommodating the variability caused by ventricular beats, namely a process 1100. Process 1100 can be performed independently or process 1100 can be performed as part of a larger collection of activities. For example, process 1100 can be performed as part of process 500, namely as steps 535, 540 (FIG. 5). Various activities in process 1100 can also be performed to trigger state transitions 430, 910, 915 in state diagram 900 (FIG. 9).

The system performing process 1100 can perform the activities at 1005, 1010, 1015, 1020, 1025, 1030 as in process 1000. The system can also determine if the last three beats have been ventricular beats at decision 1105. For example, the system can determine if the last three beats are marked with a ventricular beat occurrence indicator such as that received at 1010.

If the system determines that the last three beats have been ventricular beats, the system triggers the end of the AF event at 1110 and, when appropriate, terminates a ventricular tachycardia event at 1115. The start and termination of the ventricular tachycardia event can transition the state of a system into and out of a V-TACH event, much like transitions 910, 915 in state diagram 900 (FIG. 9).

When the V-TACH event has been terminated at 1115 or when the system determines that the last three beats have not been ventricular beats at 115, the system then determines if the average of both the weighted and preset timing comparisons in the array of the most recent beats has dropped below 0.08 at decision 1120. If the average has not dropped below 0.08, the system returns to compare the recent R to R intervals with the previous R to R interval at 1005. On the other hand, when the average has dropped below 0.08, the system triggers the end of the AF event at 1125. This triggering can transition the state of a system out of an AF event, much like transition 430 in state diagram 900 (FIG. 9).

Various implementations of the systems and techniques described here can be realized in digital electronic circuitry, integrated circuitry, specially designed ASICs (application specific integrated circuits), computer hardware, firmware, software, and/or combinations thereof. These various implementations can include one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) may include machine instructions for a programmable processor, and can be implemented in a high-level procedural and/or object-oriented programming language, and/or in assembly/machine language. As used herein, the term "machine-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing environment that includes a back-end component (e.g., as a data server), or that includes a middleware component (e.g., an application server), or that includes a front-end component (e.g., a client computer having a graphical user interface or a Web browser through which a user can interact with an implementation of the systems and techniques described here), or any combination of such back-end, middleware, or front-end components. The components of the environment can be interconnected by any form or medium of digital data communication (e.g., a communication network). Examples of communication networks include a local area network ("LAN"), a wide area network ("WAN"), and the Internet.

The computing environment can include clients and servers. A client and server are generally remote from each other and typically interact through a communication network. The relationship of client and server arises by virtue of computer programs running on the respective computers and having a client-server relationship to each other.

A number of implementations have been described. Nevertheless, it will be understood that various modifications may be made. Cardiac signals other than scalar electrocardiograms such as heart sounds can be monitored. Other weighting approaches and transformation functions can be used, depending upon the manner in which the timing of beats is compared. Weight 705 can be interpolated in any of a number of different ways such as a cubic spline between points 715, 720, 725, 730, 735. Cardiac monitoring can be performed in real time or delayed. The values of different parameters can be changed and useful results still obtained. For example, in FIG. 7, point 735 can be repositioned to a comparison factor DRR(n) value above 0.2. Accordingly, other implementations are within the scope of the following claims.

What is claimed is:

1. A device, comprising:
    a beat detector to identify a beat-to-beat timing of cardiac activity;
    a ventricular beat detector to identify ventricular beats in the cardiac activity;
    variability determination logic to determine a variability in the beat-to-beat timing of a collection of beats;
    relevance determination logic to identify a relevance of the variability in the beat-to-beat timing to at least one of atrial fibrillation and atrial flutter; and
    an event generator to generate an event when the variability in the beat-to-beat timing is identified as relevant to the at least one of atrial fibrillation and atrial flutter in light of the variability in the beat-to-beat timing caused by ventricular beats identified by the ventricular beat detector.

2. The device of claim 1, wherein the relevance determination logic is to accommodate variability in the beat-to-beat timing caused by ventricular beats by weighting ventricular beats as being negatively indicative of the one of atrial fibrillation and atrial flutter.

3. The device of claim 1, wherein the variability determination logic is to compare times between R-waves in three successive QRS complexes to determine the variability in the beat-to-beat timing.

4. The device of claim 1, wherein:
    the variability determination logic is to represent the variability in the beat-to-beat timing as a factor that is lowest when a first time between beats is close to a second time between beats; and
    the first time immediately proceeds the second time.

5. The device of claim 4, wherein the variability determination logic is to represent the variability in the beat-to-beat timing as a factor that increases non-linearly when the absolute difference between the first time the second time grows.

6. The device of claim 4, wherein the variability determination logic is to represent the variability in the beat-to-beat timing as a factor that increases more rapidly when the first time grows less than the second time than when the first time grows greater than the second time.

7. The device of claim 1, wherein the event generator is to generate an event by performing operations comprising:
    collecting data associated with the collection of beats; and
    transmitting the data associated with the collection of beats to a remote receiver.

8. The device of claim 1, wherein the relevance determination logic comprises weighting logic to:
    weight variability at a lower end of physiological values as being substantially irrelevant to the one of atrial fibrillation and atrial flutter;
    weight variability in a midrange of physiological values as being positively indicative of the one of atrial fibrillation and atrial flutter; and
    weight variability in an upper range of physiological values as being negatively indicative of the one of atrial fibrillation and atrial flutter.

9. The device of claim 8, wherein the weighting logic is also to weight a beat identified as a ventricular beat as being negatively indicative of the one of atrial fibrillation and atrial flutter.

10. The device of claim 1, wherein the relevance determination logic comprises logic to identify the relevance of the variability using a non-linear function of a beat-to-beat interval.

11. The device of claim 1, wherein the beat detector comprises a QRS detector.

12. The device of claim 1, further comprising a sensor that includes two or more body surface electrodes subject to one or more potential differences related to cardiac activity.

13. A method comprising:
receiving information describing a timing of heart beats of an individual;
determining a first time between a first heart beat and a second heart beat of the individual, wherein the second heart beat follows immediately after the first heart beat;
determining a second time between the second heart beat and a third heart beat of the individual, wherein the third heart beat follows immediately after the second heart beat;
determining a factor reflecting the difference between the first time and the second time, wherein
the factor is lowest when the first time is close to the second time, and
the factor increases non-linearly when the absolute difference between the first time the second time grows; and
identifying at least one of an atrial fibrillation event and an atrial flutter event of the individual based on the factor.

14. The method of claim 13, wherein the factor increases more rapidly when the first time grows less than the second time than when the first time grows greater than the second time.

15. The method of claim 13, wherein:
the method further comprises weighting the factor to reflect a relevance of the factor to one of atrial fibrillation and atrial flutter; and
the identifying of the at least one of the atrial fibrillation event and the atrial flutter event is based on the weighted factor.

16. The method of claim 15, wherein weighting the factor comprises:
weighting the factor at a lower end of physiological values as being substantially irrelevant to the one of atrial fibrillation and atrial flutter;
weighting the factor in a midrange of physiological values as being positively indicative of the one of atrial fibrillation and atrial flutter; and
weighting the factor in an upper range of physiological values as being negatively indicative of the one of atrial fibrillation and atrial flutter.

17. The method of claim 13, wherein:
the method further comprise repeating the determining of the first time, the determining of the second time, and the determining of the factor for additional heart beats to generate additional factors; and
the identifying of the at least one of the atrial fibrillation event and the atrial flutter event is based on the additional factors.

18. The method of claim 17, wherein identifying the at least one of the atrial fibrillation event and the atrial flutter event of the individual based on the additional factors comprises identifying the at least one of the atrial fibrillation event and the atrial flutter event of the individual based on between 19 and 199 additional factors.

19. The method of claim 13, wherein determining the factor comprises determining DRR(n) as given by $$DRR(n) = ABS\left(\frac{RR(n, n-1)}{RR(n, n-1) + RR(n-1, n-2)} - \frac{1}{2}\right).$$

20. An article comprising one or more machine-readable media storing instructions operable to cause one or more machines to perform operations, the operations comprising:
determining a beat-to-beat variability in cardiac electrical activity;
determining a relevance of the variability over a collection of beats to one of atrial fibrillation and atrial flutter using a non-linear function of a beat-to-beat interval; and
identifying one of an atrial fibrillation event and an atrial flutter event based on the determined relevance, the event being a period in time when the information content of the cardiac electrical activity is of increased relevance to the one of atrial fibrillation and atrial flutter.

21. The article of claim 20, wherein determining the relevance comprises:
weighting variability at a lower end of physiological values as being substantially irrelevant to the one of atrial fibrillation and atrial flutter;
weighting variability in a midrange of physiological values as being positively indicative of the one of atrial fibrillation and atrial flutter;
weighting variability in an upper range of physiological values as being negatively indicative of the one of atrial fibrillation and atrial flutter; and
determining a relevance of the weighted variability to the one of atrial fibrillation and atrial flutter.

22. The article of claim 20, determining the relevance comprises:
identifying a beat of the collection as a ventricular beat, and
weighting the beat as being negatively indicative of the one of atrial fibrillation and atrial flutter.

23. The article of claim 20, wherein:
determining the beat-to-beat variability comprises determining a factor reflecting the difference between a first time between a first heart beat and a second heart beat and a second time between a second heart beat and a third heart beat;
the second heart beat follows immediately after the first heart beat; and
the third heart beat follows immediately after the second heart beat.

24. The article of claim 23, wherein:
the factor is lowest when the first time is close to the second time; and
the factor increases non-linearly when the absolute difference between the first time the second time grows.

25. The article of claim 24, wherein the factor increases more rapidly when the first time grows less than the second time than when the first time grows greater than the second time.

* * * * *

UNITED STATES PATENT AND TRADEMARK OFFICE
CERTIFICATE OF CORRECTION

| | | |
|---|---|---|
| PATENT NO. | : 7,941,207 B2 | Page 1 of 1 |
| APPLICATION NO. | : 11/674053 | |
| DATED | : May 10, 2011 | |
| INVENTOR(S) | : Lev Korzinov | |

It is certified that error appears in the above-identified patent and that said Letters Patent is hereby corrected as shown below:

Col. 12, Claim 5, line 46, delete "difference between the first time the second time grows." and insert -- difference between the first time and the second time grows. --

Signed and Sealed this
Second Day of August, 2011

David J. Kappos
*Director of the United States Patent and Trademark Office*